United States Patent
Meessen et al.

(10) Patent No.: US 6,881,862 B2
(45) Date of Patent: Apr. 19, 2005

(54) PROCESS FOR THE PREPARATION OF UREA

(75) Inventors: Jozef Hubert Meessen, Gulpen (NL); Kees Jonckers, Susteren (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/488,969

(22) PCT Filed: Sep. 26, 2002

(86) PCT No.: PCT/NL02/00627

§ 371 (c)(1), (2), (4) Date: Aug. 27, 2004

(87) PCT Pub. No.: WO03/029197

PCT Pub. Date: Apr. 10, 2003

(65) Prior Publication Data

US 2005/0004397 A1 Jan. 6, 2005

(30) Foreign Application Priority Data

Oct. 1, 2001 (NL) ............................................ 1019080

(51) Int. Cl.⁷ ............................................. C07C 273/04
(52) U.S. Cl. .......................... 564/72; 422/188; 564/67; 564/70; 564/73
(58) Field of Search ............................ 472/188; 564/67, 564/70, 72, 73

(56) References Cited

U.S. PATENT DOCUMENTS 6,284,922 B1    9/2001  Pagani

2001/0031893 A1    10/2001  Pagani

FOREIGN PATENT DOCUMENTS

EP    1036787    6/2003

*Primary Examiner*—Peter O'Sullivan
(74) *Attorney, Agent, or Firm*—Mayer Brown Rowe & Maw LLP

(57) ABSTRACT

The invention relates to a process for the preparation of urea from ammonia and carbon dioxide, which preparation takes places wholy or partly with the application of a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, wherein the gas stream coming from the top of the submerged condenser is subjected to an extra washing step before this gas stream is supplied to the high-pressure scrubber. The submerged condenser operating as such may be for example a submerged condenser of horizontal or vertical design of a falling-film high-pressure carbamate condenser transformed into a submerged condenser. The invention further relates to a process for improving and/or optimizing a urea plant as well as to a urea plant as such.

10 Claims, 2 Drawing Sheets

Figure 1/2
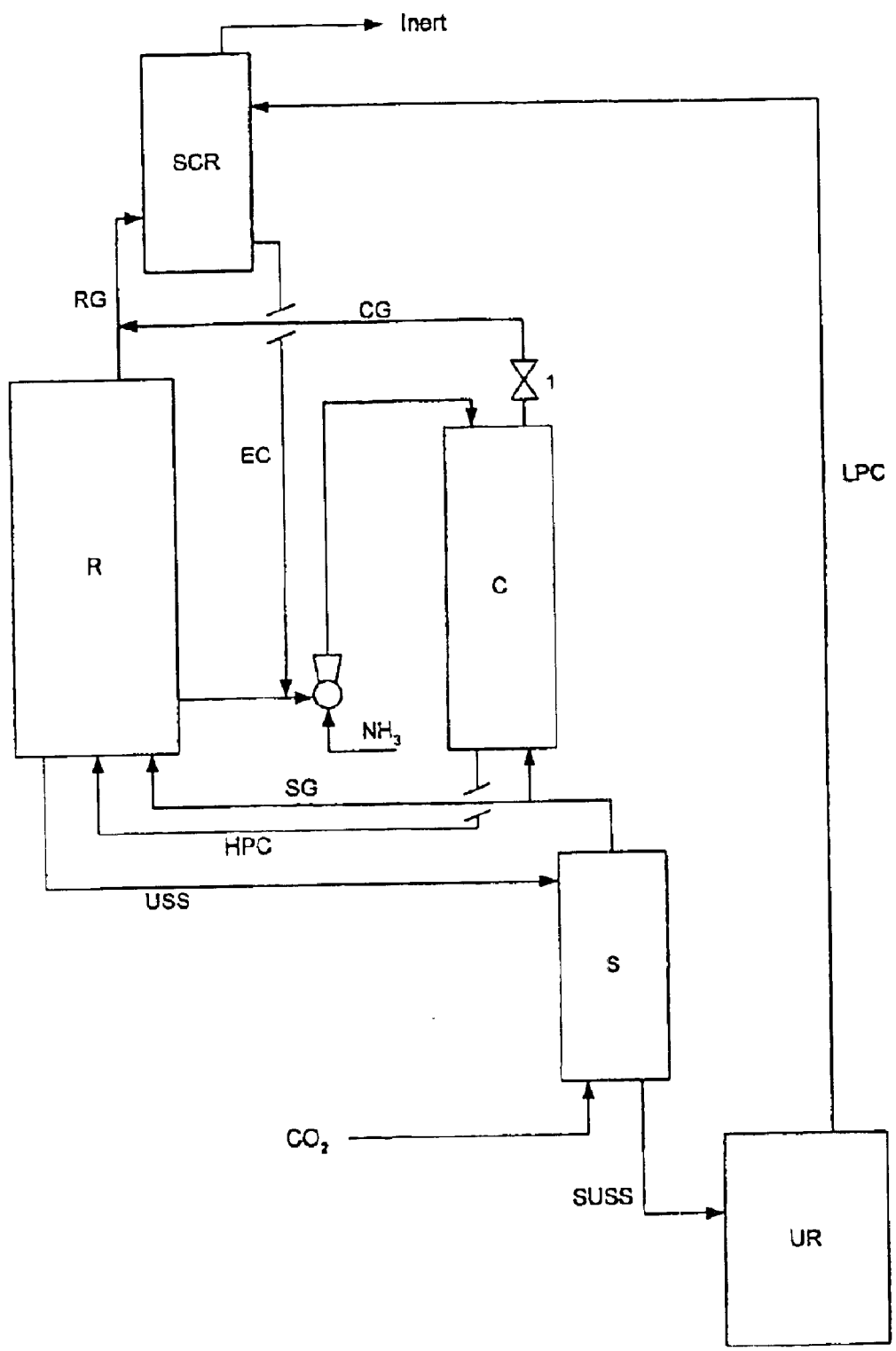

Figure 2/2
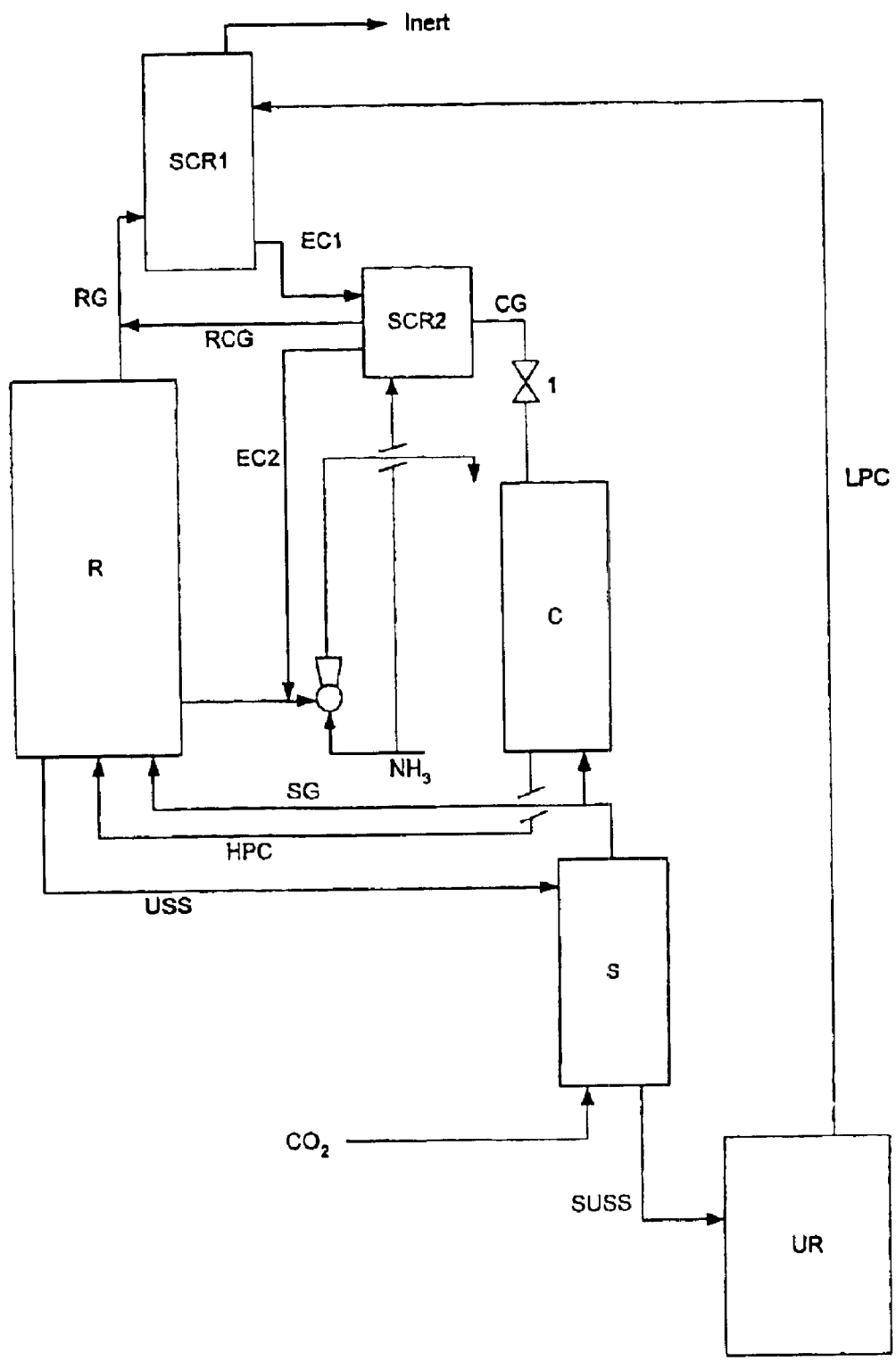

PROCESS FOR THE PREPARATION OF UREA

CROSS REFERENCE TO RELATED APPLICATION

This application is the National Phase of International Application PCT/NL02/00627 filed Sep. 26, 2002 which designated the U.S., and that International Application was published under PCT Article 21(2) in English.

The invention relates to a process for the preparation of urea from ammonia and carbon dioxide, which preparation takes places wholly or partly with the application of a synthesis reactor (hereafter also briefly referred to as "reactor"), a condenser, a washing stage or "scrubber" and a decomposition stage or "stripper", with an outlet of the stripper, through which during operation a gas mixture is discharged, being functionally connected to the inlet of the condenser and to the inlet of the reactor and with an outlet of the condenser being functionally connected to an inlet of the scrubber and with the obtained reaction mixture being stripped in countercurrent with one of the starting materials.

In a process based on the stripping principle, urea may be prepared by introducing excess ammonia along with carbon dioxide into a synthesis reactor (hereafter briefly referred to as "reactor") or synthesis zone at a suitable pressure (for example 12–40 MPa) and a suitable temperature (for example 160–250° C.), which first results in the formation of ammonium carbamate according to the reaction:

$2NH_3 + CO_2 \rightarrow H_2N-CO-ONH_4$

Dehydration of the ammonium carbamate formed then results in the formation of urea according to the equilibrium reaction:

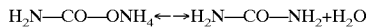

$H_2N-CO-ONH_4 \leftrightarrow H_2N-CO-NH_2 + H_2O$

The theoretically attainable conversion of ammonia and carbon dioxide into urea is determined by the thermodynamic position of the equilibrium and depends on for example the $NH_3/CO_2$ ratio (N/C ratio), the $H_2O/CO_2$ ratio and temperature.

In the conversion of ammonia and carbon dioxide to urea in the synthesis reactor, a reaction product is obtained from the synthesis reactor which product is a urea synthesis solution which consists essentially of urea, water, ammonium carbamate and unbound ammonia.

Besides a urea synthesis solution, there may evolve in the synthesis reactor a gas mixture of unconverted ammonia and carbon dioxide along with inert gases, which gas mixture is also known as synthesis gas. The inert gases present herein may originate from for example a system that adds air to the plant in order to improve the plant's corrosion resistance. For example, inert gaseous components may be supplied to the synthesis reactor via the raw materials ($NH_3$ and $CO_2$). Ammonia and carbon dioxide are removed from the synthesis gas and are preferably returned to the synthesis reactor.

The synthesis reactor may comprise separate zones for the formation of ammonium carbamate and urea. These zones may, however, also be united in a single apparatus. The synthesis may be effected in a single reactor or in two reactors. If two reactors are employed, the first reactor, for example, may be operated with virtually fresh raw materials and the second with raw materials that are completely or partly recirculated from for example the urea recovery section.

The conversion of ammonium carbamate into urea and water in the synthesis reactor may be effected by ensuring a sufficiently long residence time for the reaction mixture in the reactor. The residence time will in general be longer than 10 min, preferably longer than 20 min. The residence time will in general be shorter than 3 hours, preferably shorter than 1 hour.

A urea plant operating on the stripping principle is understood to be a urea plant in which the decomposition of the ammonium carbamate that is not converted into urea and the expulsion of the customary excess ammonia largely take place at a pressure that is essentially virtually equal to the pressure in the synthesis reactor. This decomposition/expulsion takes place in a stripper downstream of the synthesis reactor with addition of heat and with or without addition of a stripping gas. In a stripping process, carbon dioxide and/or ammonia may be used as stripping gas before these components are added to the synthesis reactor. It is also possible to use thermal stripping here, which means that ammonium carbamate is decomposed exclusively by supplying heat and the ammonia and carbon dioxide present are removed from the urea solution. Stripping may be effected in two or more steps. In a known process a first, purely thermal stripping step is followed by a $CO_2$ stripping step with further addition of heat. The ammonia and carbon dioxide-containing gas stream exiting from the stripper is returned to the reactor whether or not via a condenser.

In a urea stripping plant the synthesis reactor is operated at a temperature of 160–240° C., preferably at a temperature of 170–220° C. The pressure in the synthesis reactor is 12–21 MPa, preferably 12.5–19.5 MPa. The N/C ratio in the synthesis reactor in a urea stripping plant is between 2.5 and 4.

A frequently used embodiment for the preparation of urea by a stripping process is the Stamicarbon® $CO_2$ stripping process as described in *Uhlmann's Encyclopedia of Industrial Chemistry*, Vol. A 27, 1998, pages 344–346.

After the stripping operation, the pressure of the stripped urea synthesis solution is reduced to a low level in the urea recovery section and the solution is concentrated by evaporation, after which urea is released and a low-pressure ammonium carbamate stream is recirculated to the synthesis reactor. Depending on the process, this ammonium carbamate may be recovered in either a single or a plurality of process steps operating at different pressures.

The larger part of the gas mixture obtained in the stripping treatment is condensed and adsorbed together with the ammonia needed for the process in a condenser, following which the resulting ammonium carbamate is transferred to the synthesis reactor for the formation of urea. In a standard Stamicarbon® $CO_2$ stripping plant the carbamate condenser operating at high pressure is usually designed as a so-called falling-film condenser. Here, the liquid flows down the inside surface of the tubes of this heat exchanger as a film, with the stripping gas flowing past it in countercurrent.

An improved design of the carbamate condenser is the so-called "submerged condenser" as described in NL-A-8400839. In comparison with the conventional falling film condenser, this type of condenser has the advantage that the liquid as a rule has a longer residence time, resulting in extra urea formation in the condenser, which increases the total plant production capacity without any substantial investment. The submerged condenser, in horizontal form also known as "pool condenser", may be placed horizontally or vertically.

EP-A-1036787 describes a process for modernizing a urea plant wherein the existing falling-film condenser is transformed into a submerged condenser. To that end, an overflow weir is installed for the liquid phase in such a way that the condenser is filled with liquid when the plant is in operation. The liquid is passed to the synthesis reactor via a weir. By introducing the gas stream from the stripper in the bottom of the condenser and having the discharge take place via the top, the whole operates as a submerged condenser. The main advantage of such a process is improved heat transfer in the process. Consequently, the urea reaction may start spontaneously, permitting either another temperature increase (by about 170° C. to 183° C. because of the composition) or a higher steam pressure or a higher plant load. A combination of these advantages may also be achieved.

A known drawback of the use of a submerged condenser is that the pressure drop across the condenser that is caused by the process is greater than when a falling-film condenser is used. The gas mixture undergoing submerged condensation will undergo a pressure drop at least equal to the height of the liquid column through which the gas bubbles. This usually means a pressure drop of 10–15 metres' liquid column. However, the driving force in the synthesis loop of an existing plant, that is, the loop that connects the high-pressure equipment and is formed by the combination of stripper-condenser-reactor-stripper, is only 8–10 metres' liquid column. Since the pressure drop of the gas in the condenser is greater than the driving force in the synthesis loop, the gas phase exiting from the condenser can no longer take part in this main circulation.

In EP-A-1036787 this problem is resolved by passing the gas from the condenser to a high-pressure scrubber. In the high-pressure scrubber the condensable components that are passed from the condenser to the high-pressure scrubber are absorbed in the carbamate stream coming from the urea recovery section. This means, however, that far-reaching condensation is needed in the submerged condenser, because otherwise the high-pressure scrubber will be overloaded. Experience has taught that it is permissible for the gas from the condenser, which also contains the inert gases, to contain less than 5–10% non-condensable gases. As a result, the advantage described in EP-A1036787 is lost to a significant extent if the existing scrubber is used.

The object of the present invention is to provide an improved process for the preparation of urea with the application of a submerged condenser operating as such, wherein the problem of the relatively large pressure drop across the condenser is completely eliminated or eliminated to a significant extent.

According to the invention it has surprisingly been found that the aforementioned drawback may be resolved by subjecting the gas stream coming from the top of the submerged condenser operating as such to an extra washing step before this gas stream is passed to the high-pressure scrubber.

The term 'submerged condenser operating as such" as used in this description includes all types of submerged condenser, of both horizontal and vertical design, and falling-film condensers transformed into submerged condensers, for example the type described in EP-A-1036787.

The extra washing step mentioned is suitably effected in a second scrubber preferably positioned between the gas outlet of the submerged condenser operating as such and the high-pressure scrubber, hereafter also referred to as the first scrubber. As a washing fluid in the extra washing step mentioned use may be made of fresh ammonia and/or the carbamate solution flowing from the high-pressure scrubber to the submerged condenser operating as such. It is advantageous, however, to perform the washing step using both washing fluids mentioned. It is particularly advantageous to wash the gas first with the carbamate solution and then with the ammonia. These washing steps may be conducted with the gas as the continuous phase, for example in packed beds, structured packings or columns with sieve trays. It is also possible to use the fluid as the continuous phase, as is practiced in for example bubbling scrubbers. The washing step may physically be located within or outside the existing condenser.

Furthermore, this process is particularly suitable for improving and optimizing existing urea plants that include a submerged condenser operating as such by subjecting the gas stream coming from the top of the submerged condenser to an extra washing step before it is passed to the high-pressure scrubber. In this way overloading of the first scrubber may be avoided and a more efficient process is obtained. In an existing plant to be revamped the scrubber will have less off-gases so that the final washing will be cheaper and/or environmental pollution will be reduced. Additionally, in plants revamped according to the invention, the capacity of the plant as a whole will be higher, because the (first) scrubber is not in principle a limiting factor.

The invention further relates to a process for improving and/or optimising a urea plant, which urea plant essentially comprises a synthesis reactor, a condenser, a scrubber and a stripper, wherein an outlet of the stripper, through which a gas mixture is discharged during operation, is functionally connected to an inlet of the condenser and with the inlet of the reactor, and wherein an outlet of the condenser is functionally connected to an inlet of the scrubber and wherein the obtained reaction mixture is stripped in the stripper in countercurrent with one of the starting materials, wherein the gas stream coming from the top of the submerged condenser is subjected to an extra washing step before this gas stream is supplied to the scrubber.

The invention also relates to a urea plant comprising a high-pressure section essentially consisting of a synthesis reactor, a submerged condenser operating as such, a first scrubber and a stripper, wherein an outlet of the condenser is functionally connected to an inlet of the first scrubber, wherein a second scrubber is positioned between the said outlet of the condenser and the said inlet of the first scrubber, wherein an extra washing step of the gas stream coming from the condenser is performed. The submerged condenser operating as such preferably is a submerged condenser, of horizontal or vertical design, or a falling-film high-pressure carbamate condenser transformed into a submerged condenser.

The principle of the invention described above may be applied in all current urea stripping processes. It is clear that modifications and adaptations are possible; such modifications and adaptations are within the realm of knowledge of the average expert in this area.

Examples of urea stripping processes wherein the invention may be practiced are the Stamicarbon® $CO_2$ Stripping process, the Ammonia Stripping process, the Self-Stripping process, the ACES process (Advanced process for Cost and Energy Saving) the IDR (Isobaric-Double Recycle) process.

By way of example the invention will now be explained in further detail, without the scope of invention being limited in any way, with reference to the following figures.

FIG. 1 is a schematic representation of a part of a urea plant according to the state of the art, for example as described in EP-A-1 036 787.

FIG. 2 is a schematic representation of a part of a urea plant according to the present invention.

In FIG. 1, R represents a reactor essentially as described in EPA-1 038 787, wherein carbon dioxide and ammonia are converted into urea. The urea synthesis solution (USS) coming from the reactor is passed to a $CO_2$ stripper (S) wherein the USS is converted into a gas stream (SG) and a liquid stream (SUSS) by stripping the USS with $CO_2$. The gas stream (SG) coming from the $CO_2$ stripper consists essentially of ammonia and carbon dioxide, which is partly returned to the reactor (R) and partly to the condenser (C). The stream that contains the stripped urea synthesis solution (SUSS) is passed to the urea recovery (UR), where urea (U) is liberated and water (W) is discharged (U and W are not shown). In the UR there is obtained a low-pressure ammonium carbamate (LPC) stream, which is recycled to the high-pressure scrubber (SCR). In this (first) scrubber, the LPC is contacted with the gas stream (RG) coming from the reactor, which stream essentially consists of ammonia and carbon dioxide but additionally contains the inerts (non-condensable components) present in the carbon dioxide feedstock and ammonia feedstock. The enriched carbamate stream (EC) coming from the SCR is optionally combined with a stream that may come from the reactor and is passed, via an ammonia-driven ejector, to the high-pressure carbamate condenser (C) wherein the SG stream from the stripper is condensed with the aid of EC. The resulting high-pressure carbamate stream (HPC) is returned to the reactor and the gas stream (CG) coming from the condenser is in this case combined with the gas stream from the reactor (RG) to the high-pressure scrubber. In this example, the fresh ammonia is supplied to the high-pressure carbamate condenser (C) via an ejector but may of course also be supplied elsewhere in the R→S→C→R loop or in the R→SCR→C→R loop.

FIG. 2 shows an improvement on the state of the art in accordance with the invention, wherein a second scrubber (SCR2) is included in the conduit from the gas outlet of the condenser (CG) to the high-pressure scrubber (SCR1), wherein an extra washing step is performed. As illustrated in this example, the extra washing step is performed with fresh ammonia and with carbamate solution (EC1) originating from the high-pressure carbamate condenser (SCR1). The carbamate stream (EC2) originating from the second scrubber (SCR2) is supplied to the condenser (C) via an $NH_3$-driven ejector and the gas stream RCG is in this case combined with the gas stream from the reactor (RG) and is supplied to the high-pressure carbamate scrubber (SCR1).

It will be clear that a number of variants and modifications of the present invention and the described embodiment are possible that are within the realm of one skilled in the art on the basis of this description and their expertise. Such variants are all within the scope of the present invention and are defined by the following claims.

What is claimed is:

1. Process for the preparation of urea from ammonia and carbon dioxide, which preparation takes places wholly or partly with the application of a synthesis reactor, a condenser, a scrubber and a stripper, wherein an outlet of the stripper, through which a gas stream is discharged during operation, is functionally connected to the inlet of the condenser and to the inlet of the reactor and wherein an outlet of the condenser is functionally connected to an inlet of the scrubber and wherein the obtained reaction mixture is stripped in the stripper in countercurrent with one of the starting materials, characterized in that the gas stream coming from the top of the submerged condenser is subjected to an extra washing step before it is supplied to the scrubber.

2. Process according to claim 1, wherein, the submerged condenser operating as such is a submerged condenser or a falling-film condenser transformed into a submerged condenser.

3. Process according to claim 1, wherein the wash fluid used in the extra washing step is fresh ammonia.

4. Process according to claim 1, wherein the wash fluid used in the extra washing step is the carbamate solution flowing from the high-pressure scrubber to the condenser.

5. Process according to claim 1, wherein the gas stream is subjected to an extra washing step with both fresh ammonia and the carbamate solution.

6. Process according to claim 5, wherein the gas stream is washed first with the carbamate solution and then with fresh ammonia.

7. Process for improving and/or optimising a urea plant, which plant essentially comprises a synthesis reactor, a condenser, a scrubber and a stripper, wherein an outlet of the stripper, through which a gas mixture is discharged during operation, is functionally connected to an inlet of the condenser and with the inlet of the reactor, and wherein an outlet of the condenser is functionally connected to an inlet of the scrubber and wherein the obtained reaction mixture is stripped in the stripper in countercurrent with one of the starting materials, characterized in that the gas stream coming from the top of the submerged condenser is subjected to an extra washing step before this gas stream is supplied to the scrubber.

8. Process according to claim 7, wherein the submerged condenser operating as such is a submerged condenser, of horizontal or vertical design, or a falling-film high-pressure carbamate condenser transformed into a submerged condenser.

9. Urea plant comprising a high-pressure section essentially consisting of a synthesis reactor, a submerged condenser operating as such, a first scrubber and a stripper, wherein an outlet of the condenser is functionally connected to an inlet of the first scrubber, characterized in that a second scrubber is positioned between the said outlet of the condenser and the said inlet of the first scrubber, wherein an extra washing step of the gas stream coming from the condenser is performed.

10. Urea plant according to claim 9, wherein the submerged condenser operating as such is a submerged condenser, of horizontal or vertical design, or a falling-film high-pressure carbamate condenser transformed into a submerged condenser.

* * * * *